United States Patent [19]

Kline, Jr.

[11] Patent Number: 6,104,300

[45] Date of Patent: Aug. 15, 2000

[54] FILL TUBE ALARM SYSTEM

[76] Inventor: William F. E. Kline, Jr., 455 Nemoral St., Warminster, Pa. 18974

[21] Appl. No.: 09/360,587

[22] Filed: Jul. 26, 1999

[51] Int. Cl.⁷ ................................................ G08B 21/00
[52] U.S. Cl. ...................................... 340/627; 200/61.09
[58] Field of Search .................................. 340/603, 607, 340/627, 450; 200/61.09

[56] References Cited

U.S. PATENT DOCUMENTS

| | | | |
|---|---|---|---|
| 4,100,491 | 7/1978 | Newman, Jr. et al. | 340/631 |
| 4,205,904 | 6/1980 | Skubich et al. | 340/631 |
| 5,118,410 | 6/1992 | Rumberger | 340/631 |
| 5,174,892 | 12/1992 | Davis | 210/131 |
| 5,196,112 | 3/1993 | Eichman | 210/171 |
| 5,228,990 | 7/1993 | Chiang | 210/223 |
| 5,384,535 | 1/1995 | Mayeur | 340/631 |
| 5,402,113 | 3/1995 | Naas | 340/631 |
| 5,476,582 | 12/1995 | Camping | 210/85 |
| 5,742,234 | 4/1998 | Owen | 340/631 |
| 5,811,000 | 9/1998 | Schäfer et al. | 210/223 |

*Primary Examiner*—Nina Tong
*Assistant Examiner*—Daniel Prévl
*Attorney, Agent, or Firm*—Henderson & Sturm LLP

[57] ABSTRACT

An alarm system 10 for the fill tube 20 of an engine oil fill tube for heavy equipment to warn the operator of the equipment that an attempt has been made to sabotage the equipment by the introduction of metal particles 100 through the inlet end 22 of the engine oil fill tube 20. The alarm system 10 includes a non-metallic electrical contact member 42 having a magnetic tip 43 disposed proximate to the angled face 41 of a plate member 48 disposed within the fill tube 20. The accumulation of metal particles 100 on the plate member 40 will establish an electrical connection between the plate member and the magnetic tip 43 to activate one or more alarm members 50, 70.

10 Claims, 2 Drawing Sheets

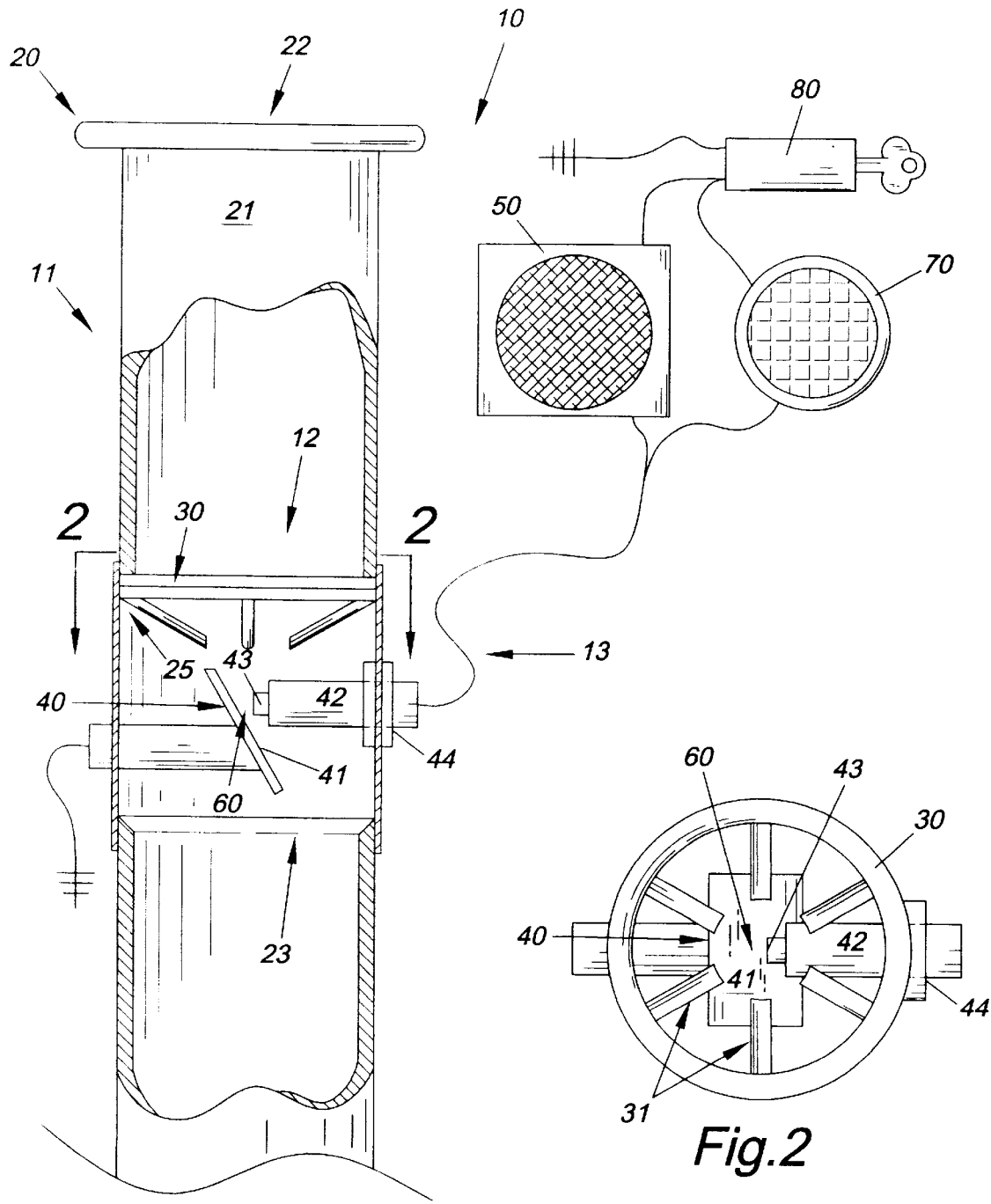

FILL TUBE ALARM SYSTEM

BACKGROUND OF THE INVENTION

1. Field of the Invention

The present invention relates to the field of engine oil and heavy equipment engines in general, and in particular to a magnetic based alarm system built into engine oil fill tubes to detect metal particles before they are pumped throughout an engine and to warn an equipment operator of the presence of the particles.

2. Description of Related Art

As can be seen by reference to the following U.S. Pat. Nos. 5,174,892; 5,196,112; 5,228,990; 5,476,582; and U.S. Pat. No. 5,811,000, the prior art is replete with myriad and diverse fuel filtering systems that are designed to trap and/or otherwise remove magnetically attractive particles from a fuel delivery system.

While all of the aforementioned prior art constructions are more than adequate for the basic purpose and function for which they have been specifically designed, they are uniformly deficient with respect to their failure to provide a simple, efficient, and practical alarm system that is placed at the engine fill tube to warn the operator of the equipment of the presence of metal shavings in the engine.

As most owners and operators of heavy equipment such as bulldozers, backhoes, graders, and the like are all too acutely aware, a dangerous trend has begun wherein metal shavings/particles have been introduced into the engine crankcases of the heavy equipment to sabotage their operation and cause irreparable harm to the equipment.

As a consequence of the foregoing situation, there has existed a longstanding need in the heavy equipment industry for a new type of anti sabotage warning system that can be installed in engine fill tubes to alert the operator of the equipment that an attempt to sabotage the equipment has taken place, and the provision of such a system is a stated objective of the present invention.

BRIEF SUMMARY OF THE INVENTION

Briefly stated, the engine oil fill tube warning system that forms the basis of the present invention comprises in general, a fill tube unit, a guide unit disposed in the upper portion of the fill tube unit, and an electromagnetic alarm unit positioned below and proximate to the guide unit.

As will be explained in greater detail further on in the specification, the fill tube unit comprises a fill tube adapter member that can be secured to the center of an existing fill tube or in the alternative could comprise a modified fill tube member that could be provided as original equipment on new engines for heavy equipment.

The guide unit comprises an annular guide member disposed within the throat of the fill tube member wherein the annular guide member is provided with a plurality of radially arrayed downwardly angled spokes which converge towards a central opening in the guide member such that metal particles will be fed by gravity towards the central opening in the guide member even if the particles were mixed in oil.

The alarm unit is disposed below the guide unit and comprises a downwardly angled plate that is positioned beneath the central opening in the guide unit and a magnetic tip and an electrical contact member positioned proximate to, but spaced from, the plate such that an accumulation of metal particles on the magnetic tip and plate will close the gap between the plate and the contact member to trigger an audible/visual alarm.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a cut away schematic view of the fill tube alarm system that forms the basis of the present invention;

FIG. 2 is a top plan view of the fill tube.

DETAILED DESCRIPTION OF THE INVENTION

Figure 3:
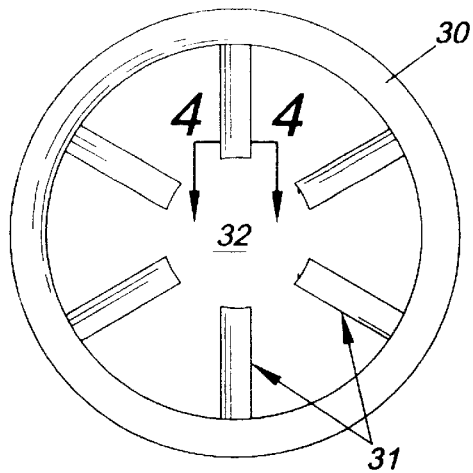
FIG. 3 is an isolated top plan view of the guide unit.

As can be seen by reference to the drawings, and in particular to FIG. 1, the fill tube alarm system that forms the basis of the present invention is designated generally by the reference number 10. The system 10 comprises in general, a fill tube unit 11, a guide unit 12, and an electromagnetic alarm unit 13. These units will now be described in seriatim fashion.

As shown in FIG. 1, the fill tube unit 11 comprises a hollow fill tube member 20 that can either be produced as original equipment in an engine oil fill tube employed in heavy equipment vehicle engines, or retro-filled into existing engine oil fill tubes in a well recognized manner. The fill tube member 20 comprises a hollow tubular body 21 having an inlet end 22 and an outlet end 23.

As can best be seen by reference to FIGS. 1 and 2, the guide unit 12 comprises a generally annular guide member 30 formed integrally with or disposed in a snap fit fashion in a suitably dimensioned peripheral recess 25 formed on the interior of the fill tube member 20 at a location intermediate the inlet end 22 and the outlet end 23 of the fill tube member 20.

Figure 4:
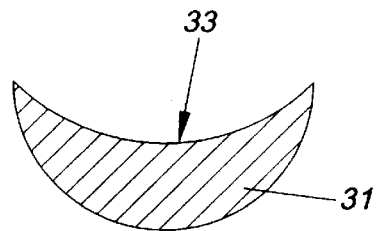
FIG. 4 is a cross sectional view taken through line 4—4 of FIG. 3.

In addition, as shown in FIGS. 1 through 4, the annular guide member 30 is provided with a plurality of downwardly angled radially arrayed spoke elements 31 which converge towards a central opening 32 formed in the annular guide member 30. Each of the spoke elements 31 have a curved upper surface 33, whose purpose and function will be described later on in the specification.

Figure 5:
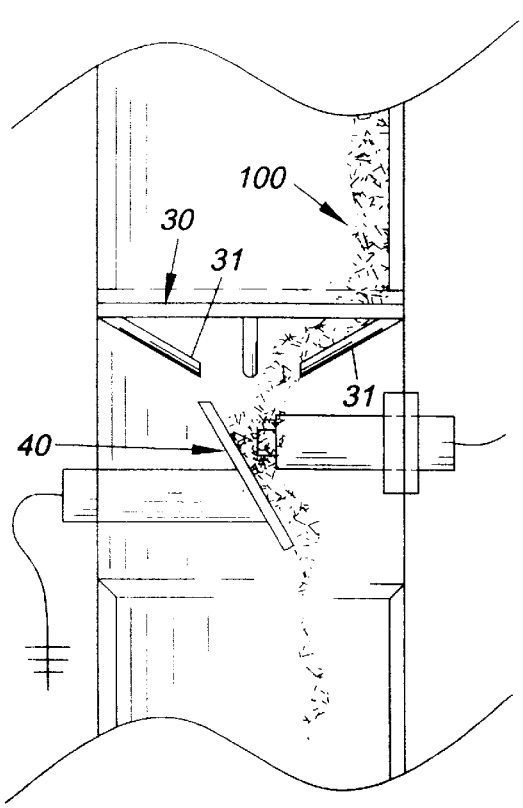
FIG. 5 is a cross sectional view showing metal filings being introduced into the fill tube.
Figure 6:
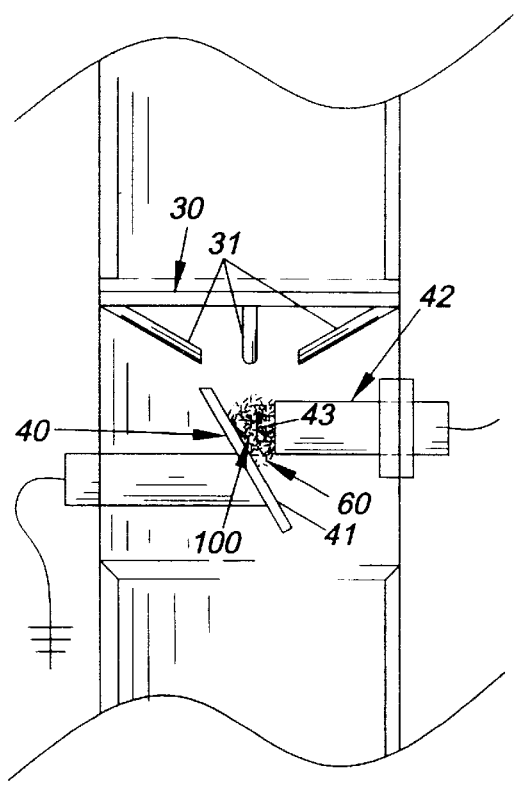
FIG. 6 is a cross sectional view showing the metal filings trapped between the plate member and the magnetic tip and electrical contact member.

Turning now to FIGS. 1, 2, 5 and 6, it can be seen that the alarm unit 13 comprises a downwardly angled electrically grounded plate member 40 mounted within the fill tube member 20 at a location below and proximate to the central opening 32 in the guide member 30.

In addition, the alarm unit 13 also includes an electrical contact member 42 having a non-metallic drilled and wired in center to the magnetic tip end 43 which is disposed proximate to, but spaced from the upwardly directed face 41 of the plate member 40 for reasons that will be explained presently.

As shown in FIGS. 1, 2, 5, and 6, the captive end 44 is an insulator for the electrical contact member 42 is secured within the fill tube member 20 and electrically coupled to a pair of alarm member 50, 70 capable of producing an audible and a visual alarm signal, respectively, when the gap 60 between the magnetic tip 43 of the contact member 42 is closed by the accumulation of metal particles/shavings 100 on the upwardly directed face 41 of the grounded plate member 40 when the equipment operator turns on the ignition switch 80.

At this juncture, it should be appreciated that in the event a person wanted to sabotage a piece of heavy equipment or other vehicle by introducing metal particles and or shavings 100 through the inlet end 22 of the engine oil fill tube 20, the curved upper surface 33 of the downwardly angled spoke elements 31 will serve to funnel the metal particles 100 towards the central opening 32 in the annular guide member 30 such that the metal particles 100 will accumulate on the angled face 41 of the grounded plate member 40 adjacent to the magnetic tip end 43 of the electrical non-metallic contact member 42.

Once the accumulation of metal particles 100 closes the gap 60 between the plate member 40, and the magnetic tip 43, the alarm members 50 and 70 will be activated once the operator turns on the ignition switch 80.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An alarm system for heavy equipment to warn the operator of the equipment that metal particles have been attempted to be introduced into the equipment engine oil system wherein the alarm system comprises:

a fill tube in fluid communication with said engine and having an inlet end and an outlet end;

a plate member disposed within the fill tube and having an angled face directed towards the inlet end of the fill tube;

a non-metallic electrical contact member disposed within the fill tube and having a magnetic tip end disposed proximate to, but spaced from the angled face of the plate member to create a gap between the magnetic tip end of the non-metallic electrical contact member and the angled face of the plate member; and alarm means responsive to the closure of the gap between the magnetic tip end of the electrical contact member and the angled face of the plate member by the accumulation of metal particles on the angled face of the plate member and magnetic tip.

2. The alarm system as in claim 1 further comprising:

guide means disposed within the fill tube at a point intermediate the inlet end of the fill tube, and the angled face of the magnetic plate member for directing metal particles onto the magnetic tip and the plate member.

3. The alarm system as in claim 1 wherein the plate member is electrically grounded.

4. The alarm system as in claim 1 wherein the alarm means includes an audible alarm.

5. The alarm system as in claim 1 wherein the alarm means includes a visual alarm.

6. The alarm system as in claim 1 wherein the alarm means includes an audible alarm and a visual alarm.

7. The alarm system as in claim 1 wherein the equipment and the alarm means are electrically connected to the ignition switch.

8. The alarm system as in claim 1 further comprising:

an annular guide member disposed intermediate the inlet end of the engine oil fill tube and the plate member wherein the guide member has an opening disposed above the angled face of the plate member and magnetic tip.

9. The alarm system as in claim 8 wherein the annular guide member has a plurality of inwardly directed spoke elements which surround said opening.

10. The alarm system as in claim 9 wherein the inwardly directed spoke elements each have a curved upper surface.

* * * * *